United States Patent
Moitzi

(10) Patent No.: US 9,528,933 B2
(45) Date of Patent: Dec. 27, 2016

(54) ADJUSTING SAMPLE HOLDER ORIENTATION FOR SYMMETRIC INCIDENT BEAM AND SCATTERED BEAM GEOMETRY TO COMPENSATE FOR REFRACTION INDEX RELATED DISTORTIONS

(71) Applicant: Anton Paar GmbH, Graz (AT)

(72) Inventor: Christian Moitzi, Raaba (AT)

(73) Assignee: Anton Paar GmbH, Graz (AT)

( * ) Notice: Subject to any disclaimer, the term of this patent is extended or adjusted under 35 U.S.C. 154(b) by 0 days.

(21) Appl. No.: 14/485,845

(22) Filed: Sep. 15, 2014

(65) Prior Publication Data

US 2015/0098086 A1 Apr. 9, 2015

(30) Foreign Application Priority Data

Oct. 8, 2013 (EP) .................................... 13187777

(51) Int. Cl.
*G01N 21/47* (2006.01)
*G01N 21/49* (2006.01)
*G01N 21/03* (2006.01)

(52) U.S. Cl.
CPC .............. *G01N 21/49* (2013.01); *G01N 21/03* (2013.01); *G01N 21/47* (2013.01); *G01N 2021/473* (2013.01)

(58) Field of Classification Search
CPC ............ B07C 5/00; C12Q 1/00; G01N 29/00; G01N 1/00; G01N 21/00; G01N 30/00; B01D 21/00

(Continued)

(56) References Cited

U.S. PATENT DOCUMENTS 4,710,643 A   12/1987   Schmukler et al.
5,104,221 A * 4/1992   Bott .................... G01N 15/0211
                                             356/336

(Continued)

FOREIGN PATENT DOCUMENTS

DE      102008007743 B3   5/2009
GB           2494734 A    3/2013

(Continued)

*Primary Examiner* — Tarifur Chowdhury
*Assistant Examiner* — Isiaka Akanbi
(74) *Attorney, Agent, or Firm* — Robert A. Blaha; Smith Tempel Blaha LLC

(57) ABSTRACT

An apparatus with an electromagnetic radiation source generates an incident-beam. A sample container accommodates a sample, receives the incident beam for interaction with the sample, and enables a scattered beam, which is to be detected, to propagate out of the sample container. An electromagnetic radiation detector detects the scattered beam which is received from the sample container. The sample container is oriented with regard to a direction of the incident beam so that an incident trajectory of the incident beam directly before propagating into the sample container up to a symmetry axis of the sample container is symmetric with a scattered trajectory of the scattered beam from the symmetry axis up to a position of the scattered beam directly after having left the sample container, such that the scattered trajectory outside of the sample container is independent of a refraction index of the sample container and of the sample.

14 Claims, 7 Drawing Sheets

(58) Field of Classification Search
USPC .................. 356/446, 336, 246, 436; 250/450
See application file for complete search history.

(56) References Cited

U.S. PATENT DOCUMENTS

| | | | |
|---|---|---|---|
| 5,129,723 A | 7/1992 | Howie et al. | |
| 5,185,641 A * | 2/1993 | Igushi | G01N 15/0211 356/336 |
| 5,572,321 A | 11/1996 | Pinier et al. | |
| 5,576,827 A * | 11/1996 | Strickland | G01N 15/0211 356/336 |
| 6,778,271 B2 * | 8/2004 | Catterall | G01N 15/0211 356/336 |
| 7,136,171 B2 * | 11/2006 | Tu | G01B 11/25 356/611 |
| 7,365,835 B2 * | 4/2008 | Wu | G01N 15/1475 356/237.1 |
| 7,532,327 B2 * | 5/2009 | Bloom | G01N 15/1459 356/337 |
| 7,916,293 B2 * | 3/2011 | Mitchell | G01N 15/1459 356/336 |
| 8,134,704 B2 * | 3/2012 | Adams | G01N 21/53 356/336 |
| 2004/0100630 A1 | 5/2004 | Yamaguchi et al. | |
| 2004/0227941 A1 * | 11/2004 | Yamaguchi | G01N 15/0205 356/336 |
| 2004/0251134 A1 | 12/2004 | Sekiwa et al. | |
| 2008/0204716 A1 * | 8/2008 | Trainer | G01N 15/0205 356/73 |
| 2009/0122315 A1 | 5/2009 | Jarrell | |
| 2011/0181869 A1 * | 7/2011 | Yamaguchi | G01N 15/0205 356/72 |

FOREIGN PATENT DOCUMENTS

| | | |
|---|---|---|
| GB | 2494735 A | 3/2013 |
| JP | H01 109245 A | 4/1989 |
| JP | H03 067154 A | 3/1991 |
| JP | 2011-053002 A | 3/2011 |
| WO | WO2011092510 A1 | 8/2011 |

* cited by examiner

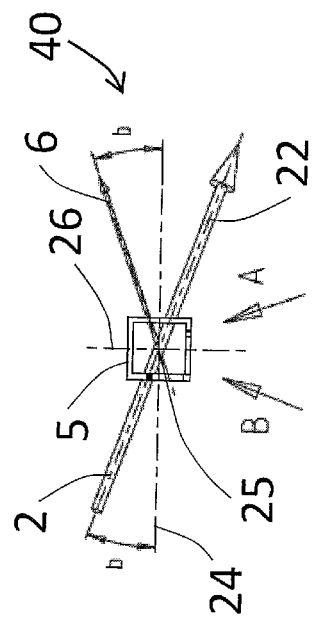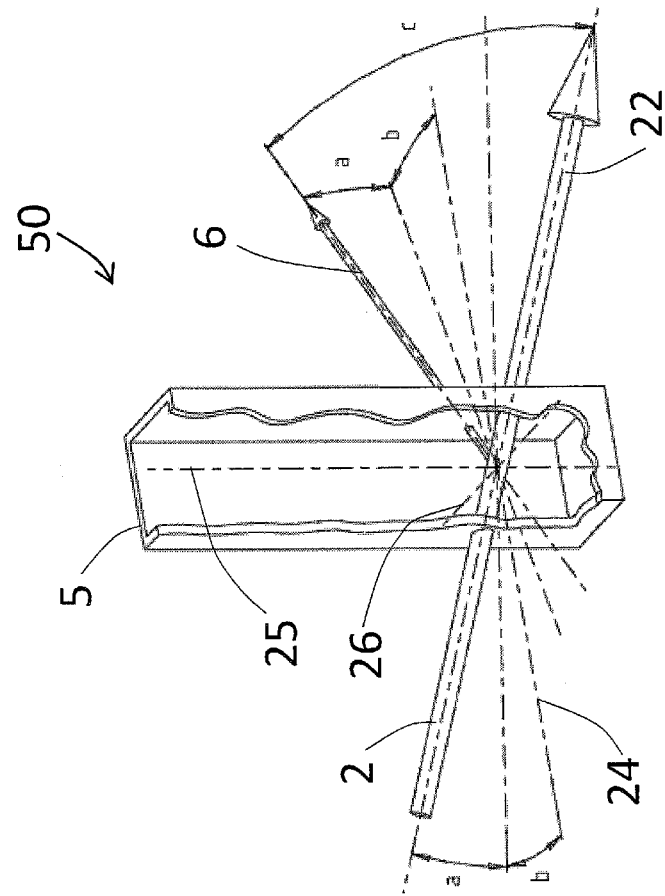
Fig. 12
Fig. 13

ADJUSTING SAMPLE HOLDER ORIENTATION FOR SYMMETRIC INCIDENT BEAM AND SCATTERED BEAM GEOMETRY TO COMPENSATE FOR REFRACTION INDEX RELATED DISTORTIONS

CROSS REFERENCE TO RELATED APPLICATION

This application claims the benefit of the filing date of European Patent Application No. 13187777, filed Oct. 8, 2013, the disclosure of which is hereby incorporated herein by reference.

TECHNICAL FIELD

The invention relates to an apparatus for analysing a sample. Furthermore, the invention relates to a method of analysing a sample.

BACKGROUND

For analyzing a fluidic sample, the fluidic sample may be filled into a sample container. An electromagnetic radiation beam may then be brought in interaction with the fluidic sample, wherein the scattered electromagnetic radiation beam may then carry information indicative of physical and/or chemical properties of the fluidic sample.

Reference is made to US 2004/100630, GB 2,494,734, DE 10 2008 007743, US 2004/251134, GB 2,494,735 and U.S. Pat. No. 4,710,643.

WO 2011/092510 discloses a cuvette for characterizing liquid samples by static and/or dynamic light scattering, having a body designed to retain a liquid sample by surface tension alone. Also provided is a light scattering instrument comprising a cuvette. Further provided is a method for preparing a cuvette containing a liquid sample, comprising the step of loading a cuvette with a liquid sample. Additionally provided is a method for characterizing a liquid sample, said method comprising the step of analyzing a liquid sample contained within a cuvette. Cuvettes may be used to retain a liquid sample and may also be used in light scattering experiments.

U.S. Pat. No. 5,572,321 relates to a device for measuring the luminous intensity scattered by thin films of colloidal media. It is more particularly intended for submicron grain-size analysis by photon correlation, and comprises a device for measuring the luminous intensity scattered by thin films of colloidal media. The device includes a monochromatic luminous source, a converging optical system focusing the source on the thin film to be analyzed, at least one photo-sensitive detector detecting the light scattered or backscattered by the thin film, and a system for processing the signal coming from one or more photodetectors.

An apparatus for electrophoretic light scattering (ELS) for measuring the zeta potential of particles in a dispersion may use an interferometric arrangement in which light scattered by the particles of the sample is superposed with a reference beam. A corresponding arrangement may also be used for determining the particle size by dynamic light scattering (DLS).

Such apparatuses can be equipped with a detection system using a fiber optic. The apparatus may be optically adjusted for a specific sample and can then be used for other samples having the same dispersion medium. However, if samples shall be analyzed which use other solvents, in particular solvents having other values of the refraction index, it is necessary to re-adjust the optics.

Commercial apparatuses, for instance Malvern Zetasizer, are equipped with specific variable compensation modules which balance out such a variation resulting from a solvent having another refraction index value. This allows a user to analyze samples having different refraction index values.

Thus, in conventional apparatuses, a change in the refraction index of sample holder and/or sample results either in a change of the trajectory of the scattered electromagnetic radiation beam leaving the sample holder, or needs to be compensated by the addition of additional optical elements. The former situation results in inaccuracies of the measurement, the latter situation results in a complex device with a high area consumption and/or is cumbersome for a user.

SUMMARY

There may be a need for a simple electromagnetic radiation based sample measurement system allowing for a high accuracy regardless of which sample container and sample are used.

According to an exemplary embodiment of the invention, an apparatus for analyzing a sample is provided, the apparatus comprising an electromagnetic radiation source configured for generating an incident electromagnetic radiation beam, a sample container configured for accommodating the sample to be analyzed, shaped to have a symmetry axis, arranged for receiving the incident electromagnetic radiation beam to propagate into the sample container for interaction with the sample, and arranged for enabling a scattered electromagnetic radiation beam, which is to be detected, to propagate out of the sample container, and an electromagnetic radiation detector configured for detecting the scattered electromagnetic radiation beam to be detected which is received from the sample container, wherein the sample container is oriented (in particular tilted, more particularly tilted by two tilting operations with two different tilting axes) with regard to a direction of the incident electromagnetic radiation beam so that an incident trajectory of the incident electromagnetic radiation beam (in particular at least along a path from a position) directly before propagating into the sample container up to the symmetry axis is symmetric with respect to a scattered trajectory of the scattered electromagnetic radiation beam, which is to be detected, (in particular at least along a path) from the symmetry axis up to a position of the scattered electromagnetic radiation beam directly after having left the sample container, such that the scattered trajectory outside of the sample container is independent of a refraction index of the sample container and of the sample.

According to another exemplary embodiment of the invention, a method of analyzing a sample is provided, wherein the method comprises directing an incident electromagnetic radiation beam onto a sample container accommodating the sample to be analyzed and being shaped to have a symmetry axis, receiving the incident electromagnetic radiation beam by the sample container to propagate into the sample container for interaction with the sample, enabling a scattered electromagnetic radiation beam, which is to be detected, to propagate out of the sample container, detecting the scattered electromagnetic radiation beam to be detected which is received from the sample container, and orienting the sample container with regard to a direction of the incident electromagnetic radiation beam so that an incident trajectory of the incident electromagnetic radiation beam directly before propagating into the sample container up to the symmetry axis is symmetric with respect to a scattered trajectory of the scattered electromagnetic radiation beam, which is to be detected, from the symmetry axis up to a position of the scattered electromagnetic radiation beam directly after having left the sample container, such that the scattered trajectory outside of the sample container is independent of a refraction index of the sample container and of the sample.

In the context of the present application, the term "symmetry axis of the sample container" may particularly denote a straight axis extending along the sample container, wherein, in each cross-sectional plane perpendicular to the symmetry axis, the cross-section of the sample container is symmetric (or at least substantially symmetric) with regard to the intersection point between the symmetry axis and the respective plane. In particular, the symmetry axis of a cylindrical sample container is constituted by its cylinder axis.

In the context of the present application, the term "symmetric trajectories" may particularly denote that, by performing a symmetry operation (such as a mirror transformation), one trajectory (i.e. incident trajectory or scattered trajectory) may be mapped on the other one (i.e. scattered trajectory or incident trajectory), and vice versa. In particular, the symmetric trajectories may be axially symmetric to one another, and more particularly may be axially symmetric to one another in two spatial protections (in particular when viewed from two orthogonal directions).

In the context of the present application, the expression "the scattered trajectory outside of the sample container is independent of a refraction index of the sample container and of the sample" may particularly denote that the propagation direction of the scattered electromagnetic radiation beam (more precisely of the part of the scattered electromagnetic radiation which is directed towards the electromagnetic radiation detector) outside of the sample container does not depend on the refraction index of the material of the sample container and/or of the material of the sample therein. It may also denote that no spatial displacements occur between different scattered electromagnetic radiation beams being scattered by different materials of different sample containers and/or of different material of different samples having different values of the refraction index.

In the context of the present application, the term "scattered electromagnetic radiation beam, which is to be detected" may particularly denote a specific portion of the scattered electromagnetic radiation resulting from an interaction between the incident electromagnetic radiation beam and the fluidic sample in the sample container, which specific portion is scattered into a predefined direction and spatial volume cell so that it impinges on an electromagnetic radiation sensitive region of the electromagnetic radiation detector. It is clear to the skilled person that, in response to irradiating the fluidic sample in the sample container with an incident electromagnetic radiation beam, electromagnetic radiation will be scattered in many directions. The selection of a single direction occurs, for instance, due to the use of special filter arrangements of the detector. Additionally or alternatively, single mode fibres may be used. However, as a consequence of the configuration of the optical path between the sample container and the electromagnetic radiation sensitive region, only and selectively the portion of the scattered electromagnetic radiation beam to be detected needs to be symmetrically arranged relative to the incident electromagnetic radiation beam.

According to an exemplary embodiment, the scattered electromagnetic radiation beam which shall be detected by the electromagnetic radiation detector can be directed precisely towards the electromagnetic radiation detector independently of the value of the refraction index of the material of the sample container and/or of the fluidic sample contained therein. This is achieved by an adjustment of the relative orientation between incident electromagnetic radiation beam and sample container (particularly by an appropriate double tilting of the electromagnetic radiation beam relative to the sample container, or vice versa) which can be performed specifically so that a symmetric beam geometry upstream and downstream of a (geometrical or scattering) center of the sample container is achieved. Thereby, a compensation of refraction index based influences of the material of the sample container and/or the material of the sample in the sample container can be accomplished. Thus, by a mere geometric orientation adjustment, and hence without any additional hardware or adjustment effort, an independency of the analysis apparatus from refraction index deviations or variations is obtained. Consequently, a user may use any desired sample container and any desired sample (which may be dissolved and/or dispersed in any desired solvent) in the analysis apparatus without the need to perform a refraction index specific adjustment before use.

EXEMPLARY EMBODIMENTS

In the following, further exemplary embodiments of the apparatus and the method will be explained.

In a preferred embodiment, given fixed angles of incidence with respect to the perpendicular to a first wall of the sample container whose walls (in particular the first wall and a second wall) are parallel to an axis of elongation (or extension) of the sample container, the electromagnetic radiation detector is positioned so as to detect a scattered electromagnetic radiation beam passing through a second wall parallel and opposite to that of the incident wall, whereby the scattered beam direction, which is received by the electromagnetic radiation detector, has angles relative to the perpendicular to the second opposite wall, which are identical to the above fixed angles of incidence, so that any changes in the refractive index of the sample or the sample container wall will produce equal and opposite changes in the angles of refraction and the first and second walls, so that the direction of detection of the scattered electromagnetic radiation beam will remain unchanged.

In a preferred embodiment, the point of intersection of the incident electromagnetic radiation beam with the sample container and the point of intersection of the scattered electromagnetic radiation beam with the sample container together with the region from which scattering occurs form a substantially isosceles triangle with region of scattering as the central angle.

In a preferred embodiment, the sample container is tilted with regard to a direction of the incident electromagnetic radiation beam so that an incident trajectory of the incident electromagnetic radiation beam directly before propagating into the sample container up to the symmetry axis is axially symmetric (or mirror symmetric) with respect to a scattered trajectory of the scattered electromagnetic radiation beam, which is to be detected, from the symmetry axis up to a position of the scattered electromagnetic radiation directly after having left the sample container, such that the scattered trajectory outside of the sample container is independent of a refraction index of the sample container and of the sample. This particularly applies to various shapes of the sample container, for instance a cylindrical shape or a cuboidal shape. Hence, there is no need for a rotational symmetry of the sample container around the axis.

In a preferred embodiment, the sample container is arranged with regard to a direction of the incident electromagnetic radiation beam so that in a first viewing direction (compare for example FIG. 3) perpendicular to a plane including the symmetry axis of the sample container (i.e. the symmetry axis lies in this plane), the incident electromagnetic radiation beam and the scattered electromagnetic radiation beam are arranged substantially axially symmetrical to one another with regard to the symmetry axis of the sample container (thus, the projection—onto this plane—of the incident electromagnetic radiation beam upstream of the symmetry axis can be mapped onto the projection—onto this plane—of the scattered electromagnetic radiation beam downstream of the symmetry axis, when viewed from the first viewing direction), and in a second viewing direction (compare for example FIG. 4) along the symmetry axis of the sample container, the incident electromagnetic radiation beam and the scattered electromagnetic radiation beam are arranged axially symmetrical to one another (thus, the projection—onto a plane perpendicular to the symmetry axis of the sample container—of the incident electromagnetic radiation beam upstream of the symmetry axis can be mapped onto the projection—onto the plane perpendicular to the symmetry axis of the sample container—of the scattered electromagnetic radiation beam downstream of the symmetry axis, when viewed from the second viewing direction). In the first viewing direction, the symmetry axis of the sample container may simultaneously constitute the symmetry axis for the axial symmetry mapping operation by which the incident electromagnetic radiation beam upstream of the symmetry axis can be mapped onto the scattered electromagnetic radiation beam downstream of the symmetry axis. In the second viewing direction, the symmetry axis of the sample container may be oriented perpendicular to and may intersect with the symmetry axis for the axial symmetry mapping operation by which the incident electromagnetic radiation beam upstream of the symmetry axis can be mapped onto the scattered electromagnetic radiation beam downstream of the symmetry axis. By a corresponding slanted or tilted arrangement between incident electromagnetic radiation beam and the symmetry axis of the sample container (and advantageously also with respect to an entrance window of the sample container through which the incident electromagnetic radiation beam enters the sample container), an independency of the detection from refraction index of the material of sample container and/or analyzed sample may be obtained, because it has turned out that the scattered electromagnetic radiation beam (i.e. the part of the scattered electromagnetic radiation to be detected by the electromagnetic radiation detector) is, after having left the sample container through an exit window thereof, substantially directed always in the same direction and substantially without spatial displacement regardless of the value of the refraction index of sample container and sample.

In a preferred embodiment, the sample container is arranged so that, in the first viewing direction (see for example FIG. 3), the symmetry axis of the sample container is tilted by an acute (i.e. an angle smaller than 90°) first tilting angle (90°−a) with regard to the direction of the incident electromagnetic radiation beam. In a preferred embodiment, the sample container is arranged so that, in the second viewing direction (see for example FIG. 4), a direction of the scattered electromagnetic radiation beam is arranged tilted by an acute (i.e. an angle smaller than) 90° second tilting angle (b+b) with regard to the direction of the incident electromagnetic radiation beam. It has turned out that, as a consequence of this double tilting, the scattered electromagnetic radiation beam to be detected can be rendered independently from the refraction index of sample and sample container. The exact values of the two tilting angles depend on the geometry of the analysis apparatus. However, upon having made an appropriate selection of these two tilting angles, no hardware based compensation of the refraction index-based effects is necessary any more. By such a double tilting, the normal direction to a symmetry plane of the sample container is tilted about two axes, in particular along the incident beam axis and perpendicular thereto, so that the refraction index compensation is obtained. A first tilting axis may correspond to the incident direction of the electromagnetic radiation beam, i.e. the optical axis. The second tilting axis may be perpendicular to this incident beam direction.

In an embodiment, the first tilting angle (90°−a) is in a range between approximately 75° and approximately 89°, in particular in a range between approximately 80° and approximately 87°. In an embodiment, the second tilting angle (b+b) is selected in a range between approximately 2° and approximately 30°, in particular in a range between approximately 6° and approximately 20°. When adjusting the values of the tilting angles, one criterion and is the need to avoid total reflection of the electromagnetic radiation beam at the sample container. Another criterion for adjusting the tilting angle is to maintain the volume of the sample container including the sample through which the electromagnetic radiation beam propagates sufficiently small. The above values of the tilting angles have turned out to be particularly appropriate for cuvettes as sample containers for an ELS analysis apparatus or an DLS analysis apparatus. Typically, for usual scattering angles (compare "c" in FIG. 13) in a range between 10° and 40° (for example 20°), it has turned out as a proper selection for each of "a" and "b" to use a range between 1° and 15°, in particular between 3° and 10°.

In an embodiment, the sample container has a polygonal shape, particularly with a rectangular, more particularly quadratic, cross section, or has a cylindrical shape with a circular cross section, in a symmetry plane perpendicular to the symmetry axis, wherein a center of gravity of the polygon or circle is located on the symmetry axis. With all these geometrical shapes, a symmetry plane can be reasonably defined which corresponds to the top surface or the bottom surface of the sample container. The entrance window and the exit window of the sample container may be corresponding (in particular parallel) surface portions of the lateral surface of the sample container. Apart from this, there are no geometrical constraints concerning the shape of the sample container.

In an embodiment, at least a sample container's volume portion which is arranged to be traversed by the electromagnetic radiation beam has a constant cross sectional shape and area perpendicular to the symmetry axis. Thus, a highly symmetric arrangement may be provided.

In an embodiment, the scattered electromagnetic radiation beam propagating towards the electromagnetic radiation detector is selected from a group consisting of a forward scattered electromagnetic radiation beam, a backwards scattered electromagnetic radiation beam, and a side scattered electromagnetic radiation beam. In a preferred embodiment, the forward scattered electromagnetic radiation beam is used for the analysis, because it is has a sufficiently high intensity and carries meaningful information indicative of properties of the sample to be analyzed. However, it is alternatively also possible to measure in back scattering geometry (see for example FIG. 8) so that the scattering electromagnetic radiation beam arrow (then constituting the measurement beam to be directed onto the electromagnetic radiation detector) propagates towards a direction upstream of the sample container, i.e. opposite to the forward scattered electromagnetic radiation beam. Also a side scattering is possible (see for example FIG. 7). Also for these cases, it is possible to render the detection independent of the refraction index of the sample container and the sample material.

In an embodiment, the apparatus comprises a mounting platform configured for mounting the sample container, wherein the mounting platform and the sample container are configured so that, when the sample container is mounted on the mounting platform, the symmetry axis is oriented parallel to the force of gravity. Such an embodiment has the advantage that the sample container is mounted on a planar, non-tilted ground and that the desired double tilting is achieved by a slanted direction of the incident electromagnetic radiation beam onto the sample container. Thus, even when the sample container is filled with a fluidic sample, is prevented that such fluidic sample flows out of the sample container due to a tilting relative to the g-vector.

In an embodiment, the apparatus comprises a beam splitter configured for splitting electromagnetic radiation generated by the electromagnetic radiation source into a first part forming the incident electromagnetic radiation beam and into a second part forming a reference beam, wherein the apparatus is configured for directing the reference beam to the electromagnetic radiation detector without interaction with the sample and is configured for bringing the scattered electromagnetic radiation beam and the reference beam into interference upstream of the electromagnetic radiation detector. Particularly for such interference-based analysis methods, it is of high importance that the geometry of the scattered electromagnetic radiation beam can be well predicted with high positional accuracy, so that the reference beam and the scattered electromagnetic radiation beam can be precisely brought in interaction with one another. This is the basis for the possibility to derive information indicative of properties of the fluidic sample to be analyzed based on an interference of the reference beam and the scattered beam.

In an embodiment, the apparatus is free of any compensation optics and any adjustment mechanism for compensating for different trajectories of scattered electromagnetic radiation beams downstream of the sample container, which different trajectories result from different refraction indexes of the sample container and/or the sample. Therefore, the apparatus can be manufactured in a compact way, and can be operated in a user friendly manner.

In an embodiment, the apparatus is configured as one of the group consisting of an Electrophoretic Light Scattering (ELS) apparatus for measuring at least one of an electrophoretic mobility of the sample, and a zeta potential of particles in the sample, and a Dynamic Light Scattering (DLS) apparatus for measuring a dimension of particles in the sample. Particularly in these interference-based measurement systems, a spatially precise superposition between reference beam and scattered electromagnetic radiation beam is of utmost importance.

In an embodiment, the apparatus comprises a source-sided beam manipulating element arranged between the electromagnetic radiation source and the sample container for manipulating the electromagnetic radiation beam upstream of the sample container to thereby direct the incident electromagnetic radiation beam onto the sample container. Such a source sided beam manipulating element can be a lens focusing the incident electrostatic radiation beam onto the sample container. Such as a lens may be oriented so that the incident electromagnetic radiation beam propagates through the lens apart from the lens center, thereby bending the incident electromagnetic radiation beam downwardly or upwardly. Then, the above described tilted configuration may be achieved without tilting the fluid-filled sample container relative to the ground.

In an embodiment, the apparatus comprises a detector-sided beam manipulating element arranged between the sample container and the electromagnetic radiation detector for manipulating the electromagnetic radiation beam downstream of the sample container to thereby direct the scattered electromagnetic radiation beam towards the electromagnetic radiation detector. Such a detector sided beam manipulating element can be a lens focusing the scattered electrostatic radiation beam towards the detector.

In an embodiment, the apparatus comprises a backscatter detector configured for detecting electromagnetic radiation backscattered from the sample container. This radiation may be detected in particular at angles of 120° to 180° with respect to the incident beam, preferably at an angle of about 175°.

In an embodiment, the electromagnetic radiation source is configured for generating an incident light beam. Therefore, electromagnetic radiation in the visible range (for instance 400 nm to 800 nm) may be used. However, alternatively, measurements can be also carried out in other wavelength regimes, such as infrared or ultraviolet.

In an embodiment, the electromagnetic radiation source is configured for generating an incident coherent electromagnetic radiation beam. Such a coherent electromagnetic radiation beam has a defined phase relation over a high spatial range, thereby allowing such an electromagnetic radiation beam to interfere with another electromagnetic radiation beam. A laser is an appropriate choice for a corresponding electromagnetic radiation source.

In an embodiment, the electromagnetic radiation detector is configured as a photodetector. This is a very simple detector being capable of deriving meaningful information indicative of properties of the sample to be analyzed from the interference result between the scattered electromagnetic radiation beam and the reference beam.

In an embodiment, the sample container is configured as a cuvette. Even relatively low quality cuvettes may be used according to exemplary embodiments without losing the high spatial accuracy. For example, a height (along the direction of the symmetry axis) of such a cuvette as sample container may be in a range between 1 cm and 5 cm, in particular 3 cm. For example, a length, width or diameter (perpendicular to the direction of the symmetry axis) of such a sample container may be in a range between 0.2 cm and 1 cm, in particular 0.5 cm.

In an embodiment, the sample container has a sample accommodation volume configured for accommodating the analyzed sample and being accessible via a top face of the sample container. Thus, the sample container can be open on the top and may thus have a cup shaped geometry. The sample may then be filled from an upper position, for instance using a pipette, into the sample container.

BRIEF DESCRIPTION OF THE DRAWINGS

The aspects defined above and further aspects of the invention are apparent from the examples of embodiment to be described hereinafter and are explained with reference to these examples of embodiment.

The invention will be described in more detail hereinafter with reference to examples of embodiment but to which the invention is not limited.

FIG. 9, FIG. 10, FIG. 11, FIG. 12 and FIG. 13 illustrate different views of a relative orientation between an electromagnetic radiation beam and a sample container of an apparatus for analyzing a sample according to exemplary embodiments of the invention.

DETAILED DESCRIPTION

Figure 1:
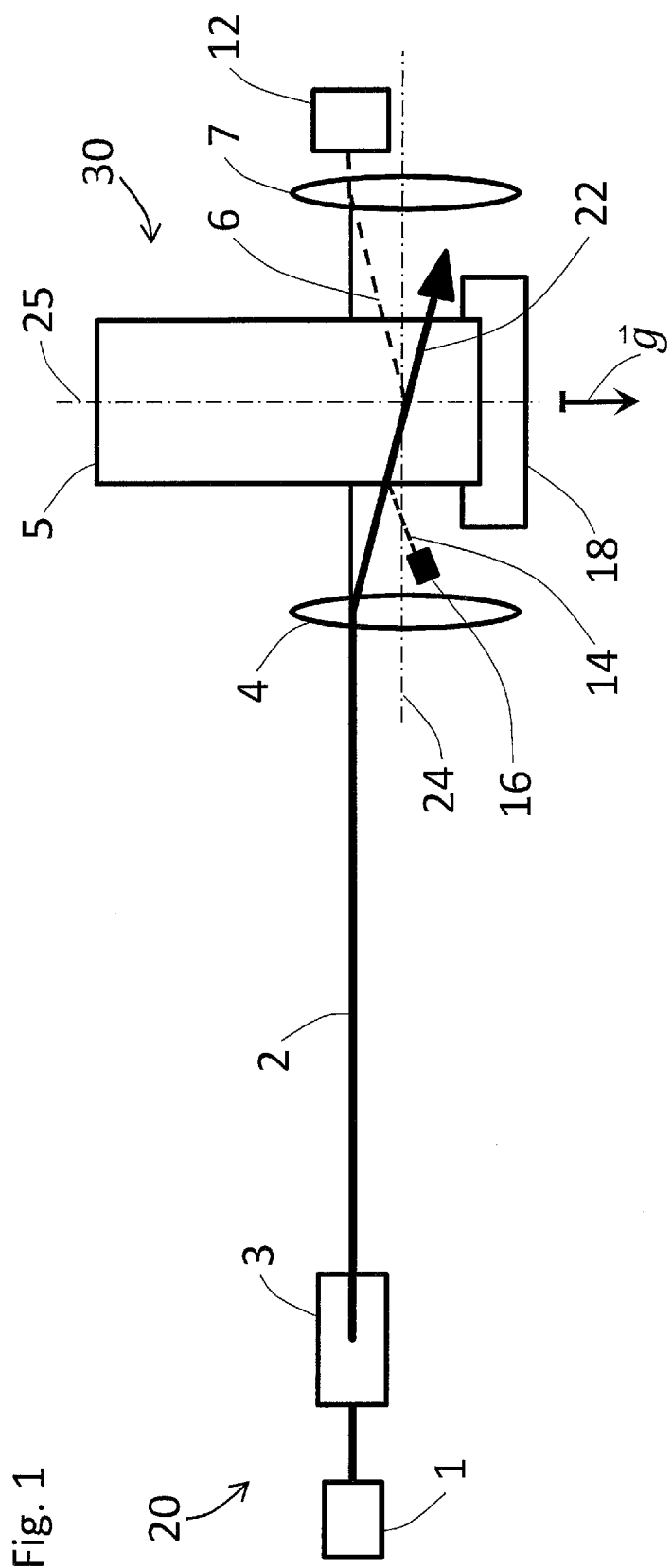
FIG. 1 illustrates a side view of an apparatus for analyzing a sample contained in a sample container being tilted with regard to an incident electromagnetic radiation beam for refraction index compensation according to an exemplary embodiment of the invention.

The illustrations in the drawings are schematical. In different drawings, similar or identical elements are provided with the same reference signs.

Before exemplary embodiments of the invention will be described referring to the figures, some basic considerations of the present invention will be described based on which exemplary embodiments have been developed.

In light scattering instruments having a detection system based on single mode fiber optics (for instance electrophoretic light scattering, ELS, or dynamic light scattering, DLS), electromagnetic radiation from only a very small spatial angular range is coupled into a detection fiber. Accordingly, only that portion of the light, which propagates along a very specific direction, is transmitted from the fiber optic towards a detector. This property of the fiber optics is in general desired, since it significantly reduces the disturbing influence of ambient light and reflections from optical members. In case of a correct adjustment of the apparatus, selectively only the scattered light from the desired volume is detected.

However, analyzing samples with different values of the refraction index are a challenge in view of the above-described boundary conditions. Depending on the refraction index of the sample, the incident and outgoing light waves are refracted in a different way. Consequently, the apparatus needs to be adjusted for each value of the refraction index of the sample individually. Otherwise, the scattered photons do not reach anymore the detector due to changed refraction angles, since these photons are no longer capable of being coupled into the fiber optic. As a consequence, the measurement signal can be lost with an increasing change of the refraction index. However, there is a need in practice that analysis apparatuses are capable of measuring samples having different values of the refraction index.

Upon using different sample containers (such as different cuvettes), being made of different materials and/or having different thicknesses of the walls of the windows, a spatial shift of the beam may occur which again can result in a loss of the measurement signal at the detector.

Conventionally, compensation plates may be inserted into the beam path which can be selected (in particular concerning the plate thickness) depending on the refraction index of the sample. This can for instance be accomplished by a motor driven change wheel having a number of different compensation plates with different thicknesses, which is cumbersome.

As mentioned above, additional optical members such as compensation plates have been conventionally used to meet the above-mentioned optical challenges, and having a thickness depending on the refraction index of the sample. This can be accomplished by a motor driven change wheel having a number of compensation plates with different thicknesses.

The above-described conventional approach has the shortcoming that additional optical components need to be implemented for compensation of refraction index based optical distortions. Moreover, a relatively large shift of the effective scattering volume in beam direction may occur, for instance 1 mm or more. The use of compensation plates furthermore allows to compensate only in steps, which results in a lack of precision. The involved motors, electronics and space contravene the trend to manufacture such apparatuses in a compact way.

In order to overcome at least a part of these shortcomings, exemplary embodiments of the invention provide an apparatus for refraction index compensation of electromagnetic radiation scattering instruments. For this purpose, a specific beam-sample container orientation geometry can be employed. By taking this measure, an automatic equilibration of the varying refraction angles (in particular due to different refraction indexes of the sample) can be obtained. Advantageously, this can be achieved without the need of an individual optical adjustment on a case by case basis or the use of separate optical compensation elements.

In an embodiment, a specific beam geometry is used which automatically balances out a spatial displacement or shift of the electromagnetic radiation beam as a result of the use of sample containers with fluidic sample having varying values of the refraction index. There is no need for a user to adjust the apparatus when the value of the refraction index of the sample container and/or fluidic sample is changed. It is also dispensable to use changeable optical components such as compensation plates. The impinging electromagnetic radiation beam and the electromagnetic radiation beam scattering out of the sample container are arranged symmetrically relative to the sample container (in particular to its center). The refraction index of the electromagnetic radiation beam when propagating into the sample container and of the scattered electromagnetic radiation beam when propagating out of the sample container mutually equilibrate one another.

According to an exemplary embodiment, this can be achieved by a specific double tilting of the sample container (more precisely of a geometric symmetry axis of the sample container) relative to the electromagnetic radiation beam. As compared to a perpendicular propagation of the incident electromagnetic radiation beam into an entrance window of the sample container, a first tilting can be made which turns the incident electromagnetic radiation beam relative to a normal vector of the entrance window towards the symmetry axis of the sample container by a first angle ("a"). Additionally, as compared to the perpendicular propagation of the incident electromagnetic radiation beam into the entrance window of the sample container, a second tilting can be made which turns the incident electromagnetic radiation beam relative to a normal vector of the entrance window within a plane perpendicular to the symmetry axis of the sample container by a second angle ("b").

This results in a propagation path of the electromagnetic radiation on its way towards the center of the sample container and on its way out of the sample container being symmetrical. Refraction index based optical effects on both sides of the center therefore compensate one another. In other words, the sample container may be tilted twice along different tilting axes in order to obtain a completely symmetric image on the source side portion and on the detector side portion of the propagation path (in particular the incident angle and the exit angle may be identical).

Such an embodiment has the advantage that samples with any desired value of the refraction index can be measured. Moreover, such embodiments only result in a very small spatial displacement of the scattering volume parallel to the entrance window of the sample container (smaller, and in some cases significantly smaller, than 0.1 mm). In beam direction, the effective scattering volume remains exactly in the center between entrance window and exit window. Furthermore, a precise and continuous or stepless compensation is possible for each refraction index rather than a mere stepwise compensation as in case of the conventional use of separate optical members such as compensation plates. Furthermore, such an embodiment can be implemented in a compact way, since separate members required conventionally for refraction index compensation (motor, change wheel, compensation plates) are dispensable and no time has to be spent for adjusting an optical path.

Figure 2:
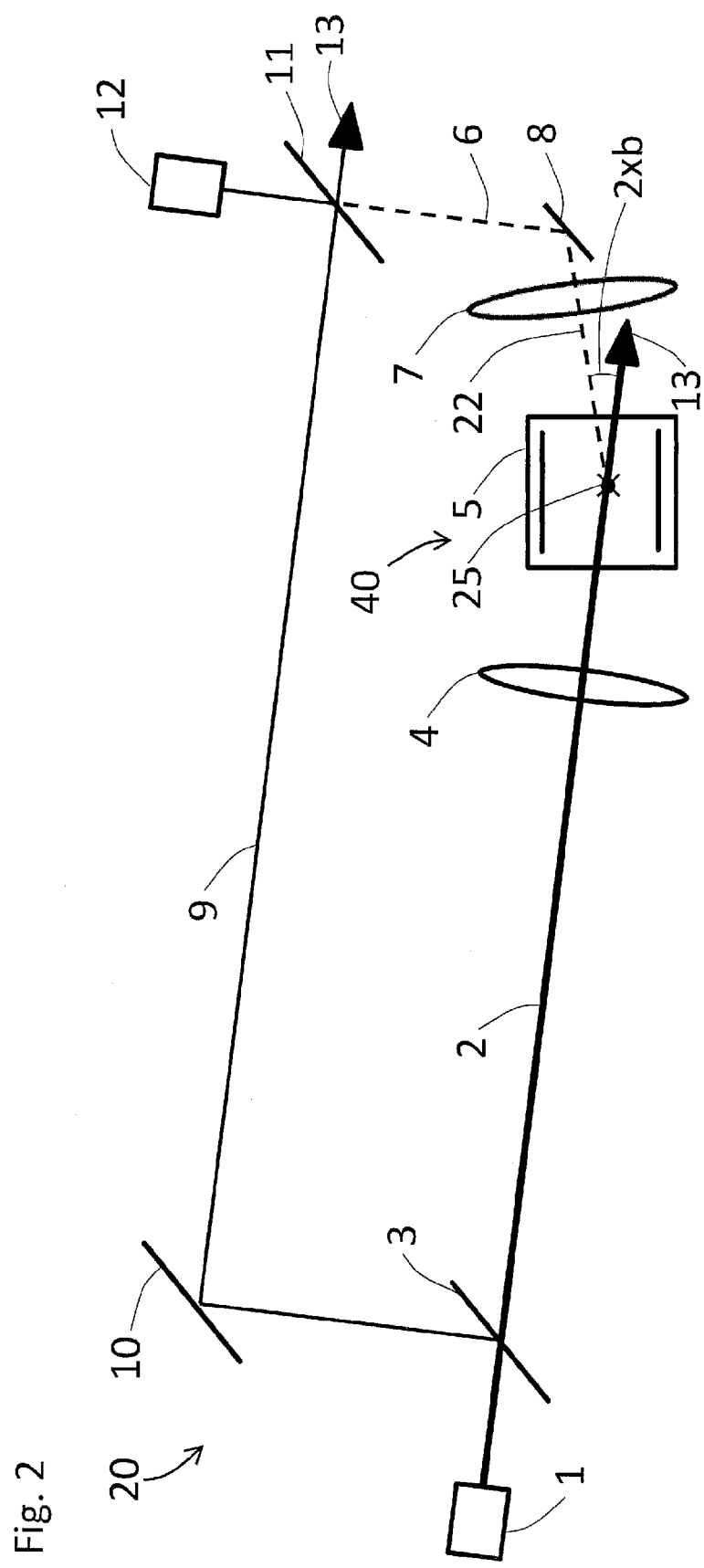
FIG. 2 illustrates a top view of the apparatus of FIG. 1.

FIG. 1 illustrates a side view of an apparatus 20 (which may be embodied as electrophoretic light scattering, ELS, apparatus for measuring a zeta potential of particles of a sample) for analyzing a fluidic sample contained in a sample container 5 being tilted around two tilting axes with regard to an electromagnetic radiation beam 2 for refraction index compensation according to an exemplary embodiment of the invention. FIG. 2 illustrates a top view of the apparatus 20 of FIG. 1. For DLS (dynamic light scattering) measurements the reference beam 9 may be omitted (however, alternatively, the reference beam 9 may be used in a DLS measurement as well).

An electromagnetic radiation source 1, here configured as a laser light source, generates electromagnetic radiation in form of collimated laser light. A beam splitter 3 splits this electromagnetic radiation beam into two parts.

A first part thereof is guided through a source sided beam manipulating element 4, configured as a lens, which focuses the first part as incident electromagnetic radiation beam 2 towards the center of the sample container 5 constituting a sample cell. Additionally, this lens bends the first part downwards (the lens is not hit by the laser beam at its central position). The manipulated first part of the generated electromagnetic radiation beam enters the sample container 5 having transparent windows and having electrodes (indicated schematically in FIG. 2) for the generation of an electric field in a fluidic sample which is accommodated in the sample container 5. As will be described below in more detail, the incident electromagnetic radiation beam 2 is then scattered by the fluidic sample within the sample container 5. The fluidic sample within the sample container 5 scatters light to all directions in space. The scattered electromagnetic radiation exits the sample container 5. A part of the scattered electromagnetic radiation, denoted as scattered electromagnetic radiation beam 6 to be detected (because it is intended to be transmitted to an electromagnetic radiation detector 12 for detection), is guided towards a detector sided manipulating element 7, here embodied as a further lens. The detector sided beam manipulating element 7 is here configured as a focusing lens with a focal point in the center of the sample container 5 and redirects the scattered electromagnetic radiation beam 6 to be detected to an optical plane of the interferometer, described below in more detail.

After the interaction with the detector sided beam manipulating element 7, the scattered electromagnetic radiation beam 6 is reflected by a mirror 8, so that the scattered electromagnetic radiation beam 6 is directed towards the electromagnetic radiation detector 12. A fiber optics, however, arranged at an entrance of the electromagnetic radiation detector 12, collects and delivers only light scattered into one particular angle to the electromagnetic radiation detector 12. This special light path is shown as dashed line in FIG. 1 and FIG. 2 and is denoted as scattered electromagnetic radiation beam 6 to be detected. The frequency of this scattered electromagnetic radiation beam 6 is shifted by the Doppler effect as the scattering particles of the fluidic sample in the sample container 5 are moving collectively in one direction. This motion is induced by the electric field generated by the electrodes within the sample container 5 and is proportional to the zeta potential of the particle surface.

The second part of the electromagnetic radiation beam divided by the beam splitter 3 and being not directed towards the sample container 5 (and being therefore free of any interaction with the fluidic sample along its entire propagation path) can be denoted as a reference beam 9, which has been separated from the remainder of the primary laser beam. The reference beam 9 is reflected by a mirror 10. An optical modulator (not shown) may be used to shift the frequency of the reference beam 9.

A beam combiner 11 combines the reference beam 9 with the scattered electromagnetic radiation beam 6 to be detected in an interferometric way, so that the beam resulting from an interference between the reference beam 9 and the scattered electromagnetic radiation beam 6 can be detected by the electromagnetic radiation detector 12. An analysis processor (not shown) is supplied with the detection signals detected by the electromagnetic radiation detector 12 and is then capable, by applying techniques which are known to a skilled person, to determine at least one property (such as the zeta potential, the electromobility, the medium particle size, etc.) of the fluidic sample in the sample container 5.

As already mentioned, the electromagnetic radiation detector 12 is here configured as a fiber optical detector which collects and detects light coming from one particular direction only, because only this light is coupled into the single mode fibers. The detected signal is the result of the interference between the scattered electromagnetic radiation beam 6 and the reference beam 9. The frequency of a resulting beat is the difference between their frequencies. The analysis processor, which may be configured as a digital signal processing unit, may be used to determine the beat frequency (i.e. the rate of phase change) and to calculate the zeta potential of the particles in the fluidic sample accommodated in the sample container 5.

Reference numeral 22 indicates the portion of the electromagnetic radiation which propagates through the entire sample container 5 without being scattered. Reference numeral 13 shows an absorber (or light trap) for absorbing or trapping electromagnetic radiation of the reference beam 9 and/or of the scattered electromagnetic radiation beam 6 not falling onto the electromagnetic radiation detector 12. Reference numeral 14 indicates back reflection of the laser beam from the entrance window of the sample container 5. Reference numeral 16 shows another optional absorber (or light trap) for absorbing or trapping the electromagnetic radiation which is reflected from an entrance window of the sample container 5 upon irradiating the latter with the incident electromagnetic radiation beam 2. Reference numeral 24 indicates a symmetry plane which visually emphasizes the symmetry of the incident electromagnetic radiation beam 2 and the scattered electromagnetic radiation beam 6 in the path between the beam manipulating elements 4, 7.

For DLS measurement without the reference beam 9 (although use of a reference beam 9 is possible for a DLS measurement as well), the scattered electromagnetic radiation beam 6 emanating the cell or sample container 5 is detected and analyzed.

According to the described embodiment of the invention, the following special features of the optic layout shall be explicitly mentioned:

i) The electromagnetic radiation beam transmits the sample in the sample container 5 not in the optical plane of the interferometer but is bent downwards by the source sided beam manipulating element 4 (here configured as a lens). This directs the back reflection (see reference numeral 14) at the entrance window of the sample container 5 towards a desired destination; and ii) The scattered electromagnetic radiation beam 6 and the incident electromagnetic radiation beam 2 are arranged in a symmetric fashion relative to the sample container 5. This means that the refraction of the incident electromagnetic radiation beam 2 at the entrance window of the sample container 5 and the scattered electromagnetic radiation 6 at the exit window are totally symmetrical. This statement is valid for all possible refraction indexes of the sample and for all materials and thicknesses of the cell wall of the sample container 5 (wherein the entrance and exit windows shall be designed identical).

The sample container 5 accommodating the sample to be analyzed is shaped to have a symmetry axis 25, is arranged for receiving the incident electromagnetic radiation beam 2 (via an entrance window) to propagate into the sample container 5 for interaction with the sample, and is arranged for enabling the scattered electromagnetic radiation beam 6 to propagate out of the sample container 5 (via an exit window).

Advantageously, the sample container 5 is oriented with regard to a direction of the incident electromagnetic radiation beam 2 so that an incident trajectory of the incident electromagnetic radiation beam 2 at least along a path from a position directly before propagating into the sample container 5 up to the symmetry axis 25 is symmetric with respect to a scattered trajectory of the scattered electromagnetic radiation beam 6 at least along a path from the symmetry axis 25 up to a position of the scattered electromagnetic radiation 6 directly after having left the sample container 5. These symmetric paths can be designed by an appropriate orientation between sample container 5 and the incident electromagnetic radiation beam 2 only, so that the scattered trajectory outside of the sample container 5 (i.e. the radiation to be detected) is independent of a refraction index of the sample container 5 and of the sample. In other words, regardless of the refraction index of the sample container 5 and the sample, the direction in which the portion of interest (i.e. the portion according to which the electromagnetic radiation detector 12 is spatially aligned and therefore exclusively sensitive to) of the scattered electromagnetic radiation propagates is always the same, even if different samples and different sample containers 5 are used within the apparatus 20.

More specifically, in order to achieve the above described symmetry and therefore independency of refraction index changes of sample and/or sample container 5, the sample container 5 is arranged with regard to the propagation direction of the incident electromagnetic radiation beam 2 so that:

in a first viewing direction 30 shown in FIG. 1 perpendicular to a plane (i.e. the paper plane of FIG. 1) including the symmetry axis 25 of the sample container 5, the incident electromagnetic radiation beam 2 (more precisely its projection on the first viewing direction 30) and the scattered electromagnetic radiation beam 6 to be detected (more precisely its projection on the first viewing direction 30) are arranged axially symmetrical to one another with regard to the symmetry axis 25 of the sample container 5 (which also forms the symmetry axis for the axial symmetry operations); and in a second viewing direction 40 shown in FIG. 2 along the symmetry axis 25 of the sample container (perpendicular to the paper plane of FIG. 2), the incident electromagnetic radiation beam 2 (more precisely its projection on the second viewing direction 40) and the scattered electromagnetic radiation beam 6 to be detected (more precisely its projection on the second viewing direction 40) are arranged axially symmetrical to one another (wherein the symmetry axis for the axial symmetry operation intersects with the symmetry axis 25 of the sample container 5).

Figure 3:
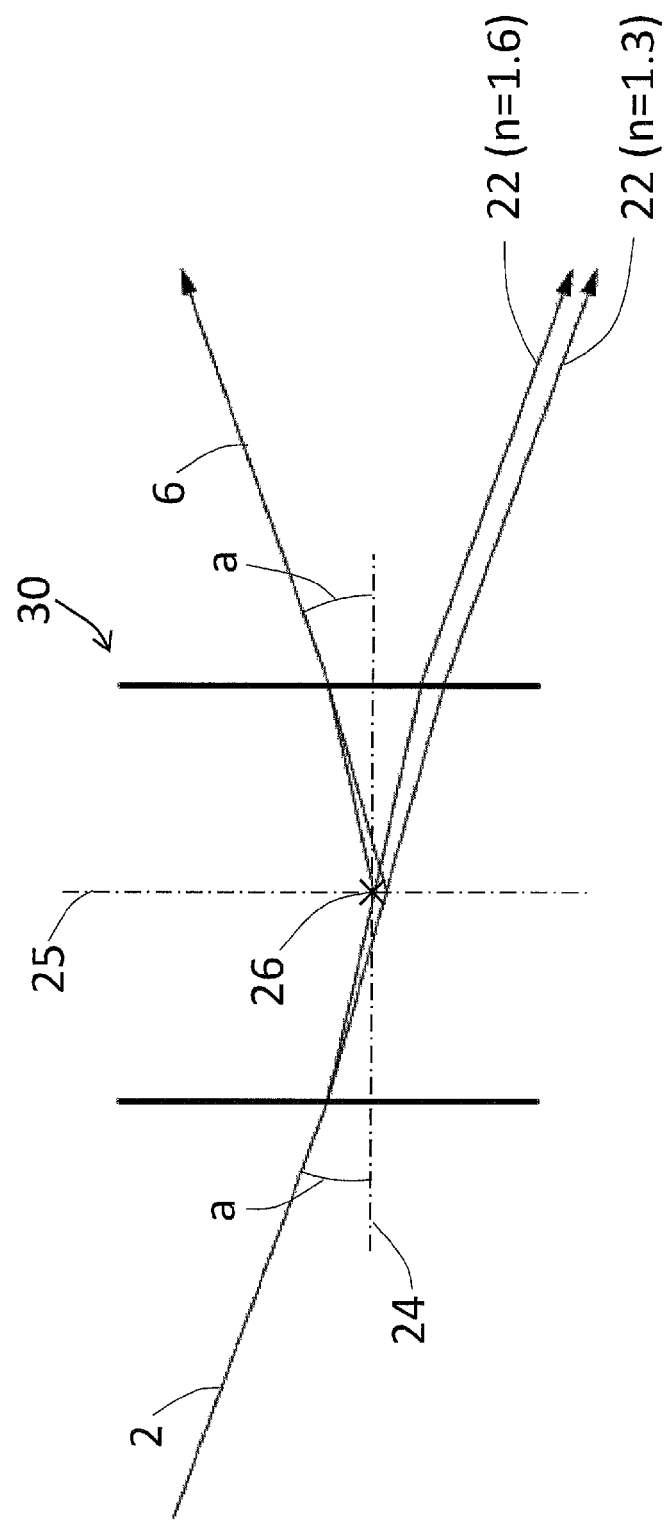
FIG. 3 illustrates a side view of the beam geometry of an electromagnetic radiation beam propagating through the apparatus of FIG. 1 and FIG. 2.
Figure 4:
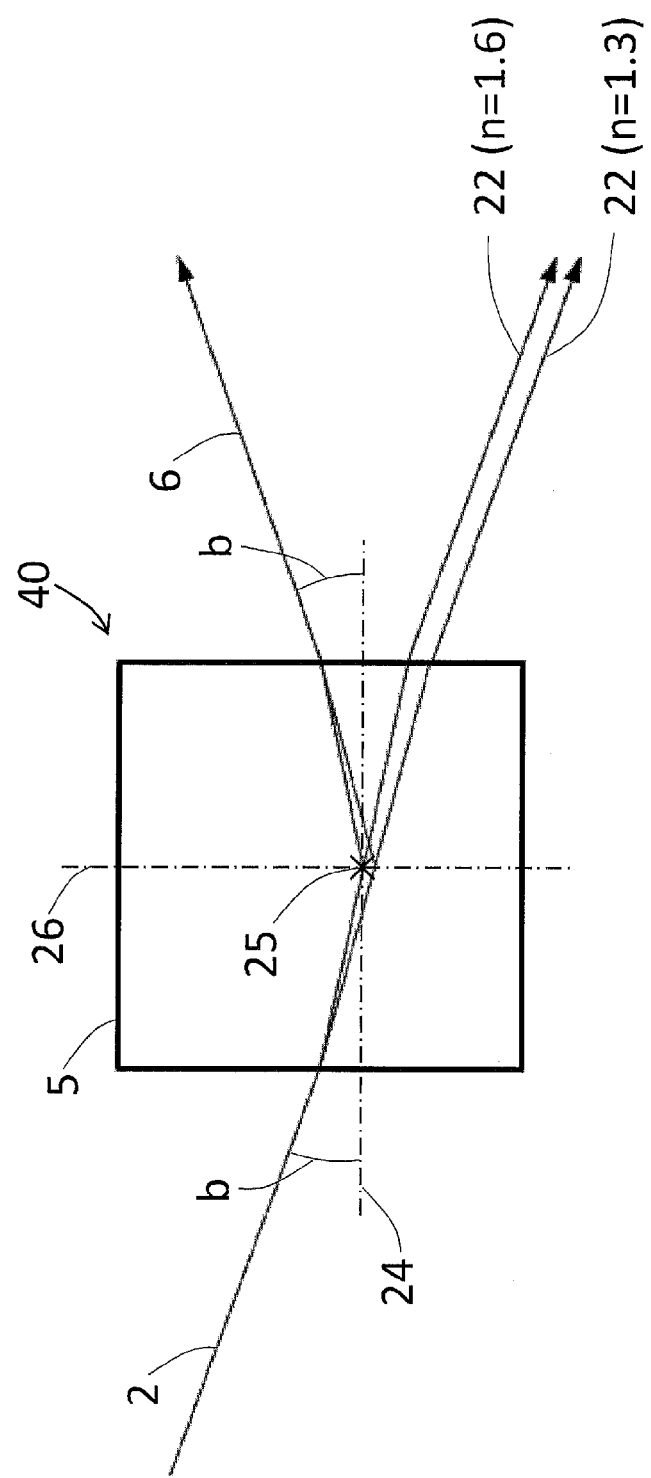
FIG. 4 illustrates a top view of the beam geometry of the electromagnetic radiation beam propagating through the apparatus of FIG. 1 and FIG. 2.

These geometric conditions, which are merely obtained by tilting the incident electromagnetic radiation beam 2 relative to sample container 5, are described in further detail referring to FIG. 3 and FIG. 4. The apparatus 20 comprises a mounting platform 18 for mounting the sample container 5, wherein the mounting platform 18 and the sample container 5 are configured so that, when the sample container 5 is mounted on the mounting platform 18, the symmetry axis 25 is oriented parallel to the force of gravity g. Thus, no slanted orientation of the sample container 5 accommodating the fluidic sample with regard to the force of gravity and therefore the ground is necessary, and the desired tilted orientation can be achieved by tilting the incident electromagnetic radiation beam 2 rather then that sample container 5.

Advantageously, the apparatus 20 is free of any compensation optics and any adjustment mechanism for compensating for different trajectories of the scattered electromagnetic radiation beams 6 downstream of the sample container 5, which different trajectories conventionally result from different refraction indexes of the sample container 5 and/or the sample.

FIG. 3 illustrates a side view of a beam geometry of the electromagnetic radiation beam propagating through the apparatus 20 according to FIG. 1 and FIG. 2. FIG. 4 illustrates a top view of the beam geometry of the electromagnetic radiation beam propagating through the apparatus 20 of FIG. 1 and FIG. 2.

As can be taken from FIG. 3, the sample container 5 is arranged so that, in the first viewing direction 30, the symmetry axis 25 is tilted by an acute first tilting angle 90°−a with regard to the direction of the incident electromagnetic radiation beam 2. The first tilting angle 90°−a can be in a range between 80° and 87°.

As can be taken from FIG. 4, the sample container 5 is arranged so that, in the second viewing direction 40, a propagation direction of the scattered electromagnetic radiation beam 6 is arranged tilted by an acute second tilting angle b+b with regard to the direction of the incident electromagnetic radiation beam 2. The second tilting angle b+b is selected in a range between 6° and 20°.

The described double tilting of the incident electromagnetic radiation beam 2 relative to the sample container 5 has two advantageous effects: On the one hand, it prevents the portion of the incident electromagnetic radiation beam 2 reflected at the entrance window of the sample container 5 from falling to an undesired position. Even more important, it results in the symmetric mutual configuration of incident trajectory and scattered trajectory (in both viewing directions 30 and 40 at the same time) which forms the basis for the significant advantage that no readjustment of the optical path downstream of the sample container 5 is required for a change of a sample container 5 and/or a sample accommodated therein, which results in a change of the refraction index. Along viewing direction 30, the symmetry axis 25 of the sample container 5 simultaneously constitutes the symmetry axis according to which the incident electromagnetic radiation beam 2 is axially symmetrically mapped onto the scattered electromagnetic radiation beam 6. Along viewing direction 40, a further symmetry axis 26, which is intersected by the symmetry axis 25 of the sample container 5, constitutes the symmetry axis according to which the incident electromagnetic radiation beam 2 is axially symmetrically mapped onto the scattered electromagnetic radiation beam 6.

Coming back to the configuration of FIG. 3, the sample container 5 is arranged vertically and is not slanted. In order to achieve the tilted arrangement described above, the laser is not aligned horizontally, but generates an electromagnetic radiation beam which is tilted with regard to a horizontal axis. A change of the refraction index results, as in conventional approaches, in a beam displacement. This is shown in FIG. 3 for different values of the refraction index (n=1.3, n=1.6). In the described embodiment, the detection does not occur in the laser plane, but symmetrically to the incident laser (mapped or mirrored at the dot-dashed line/symmetry axis 26). The scattered light is detected in an upward direction. Thus, the refraction conditions at the two windows of the sample container 5 for the incident electromagnetic radiation beam 2 and the scattered electromagnetic radiation beam 6 to be detected are identical. At different values of the scattering index, a scattered beam is detected at a slightly displaced angle in the sample (shown in FIG. 3 for different values of the refraction index (n=1.3, n=1.6)). However, outside of the sample container 5 (i.e. in air), the two scattered electromagnetic radiation beams 6 are again in perfect alignment (as a consequence of the symmetry). The only change in response to a changed refraction index results from a slight displacement of the effective scattering volume. The latter is defined as the overlapping volume of the incident electromagnetic radiation beam 2 and the scattered electromagnetic radiation beam 6 (in FIG. 3 the intersection between the two lines for the different values of n). All possible intersections are located exactly in the middle of the sample container 5 and the vertical displacement is very small (less than 0.1 mm between the two values of the refraction index (n=1.3, n=1.6) at an angle of the incident electromagnetic radiation beam 2 of 7°).

Coming now again to FIG. 4, the horizontal alignment of the entrance window is not normal to the propagation direction of the incident electromagnetic radiation beam 2. The arrangement of incident electromagnetic radiation beam 2 and scattered electromagnetic radiation beam 6 to be detected relative to the sample container 5 is, also in the second viewing direction 40 shown in FIG. 4, symmetric. Consequently, the effective scattering volume is exactly in the center or middle between entrance window and exit window of the sample container 5, for each and every refraction index of the fluidic sample. Only a very slight displacement (less than 0.1 mm) parallel to the entrance window occurs.

Figure 6:
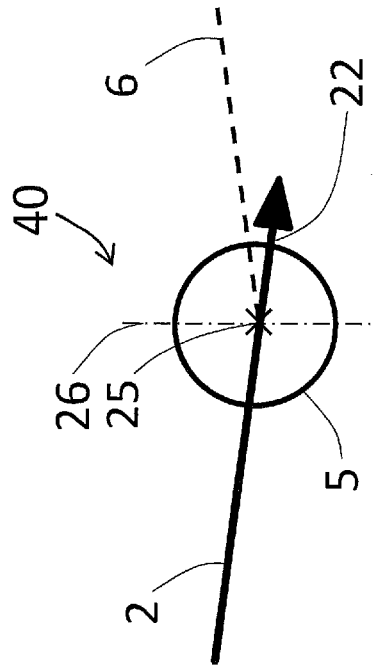
FIG. 6 illustrates an electromagnetic radiation beam geometry according to an exemplary embodiment of the invention for a circular cylindrical sample container and a forward scattering operation mode.
Figure 8:
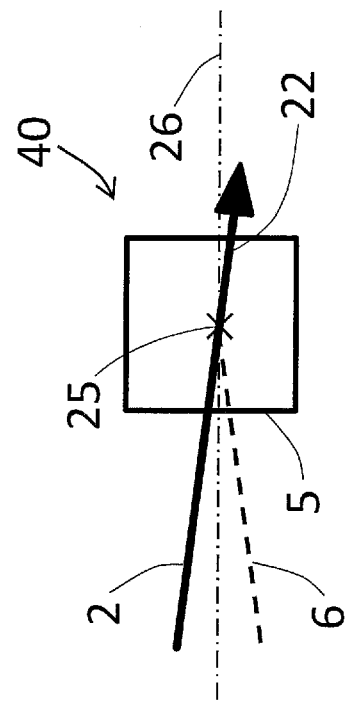
FIG. 8 illustrates an electromagnetic radiation beam geometry according to an exemplary embodiment of the invention for a cuboid sample container and a back scattering operation mode.
Figure 5:
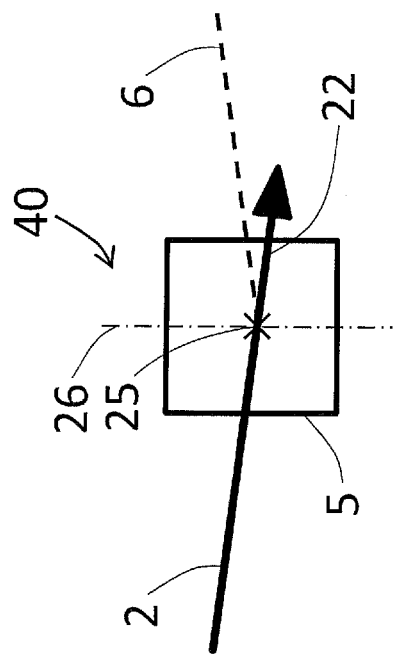
FIG. 5 illustrates an electromagnetic radiation beam geometry according to an exemplary embodiment of the invention for a cuboid sample container and a forward scattering operation mode.
Figure 7:
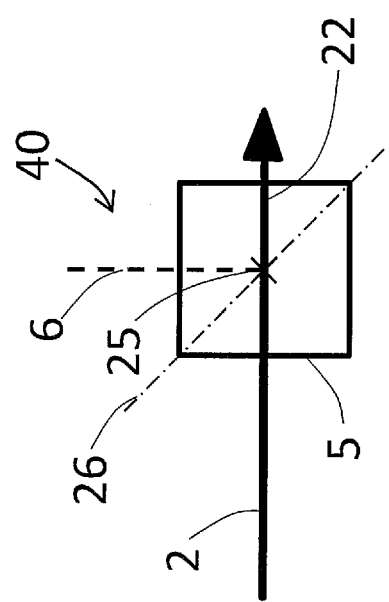
FIG. 7 illustrates an electromagnetic radiation beam geometry according to an exemplary embodiment of the invention for a cuboid sample container and a side scattering operation mode.
Figure 11:
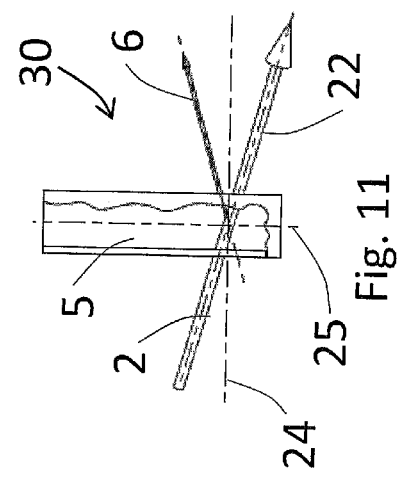
Figure 10:
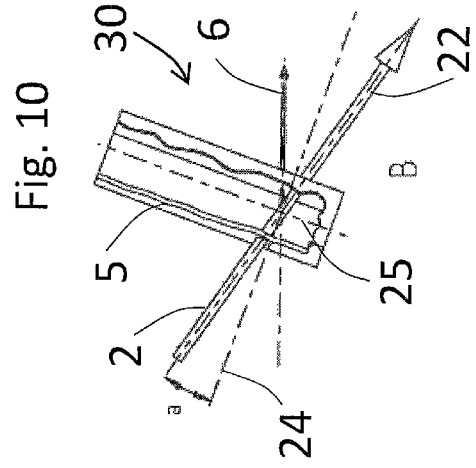
Figure 9:
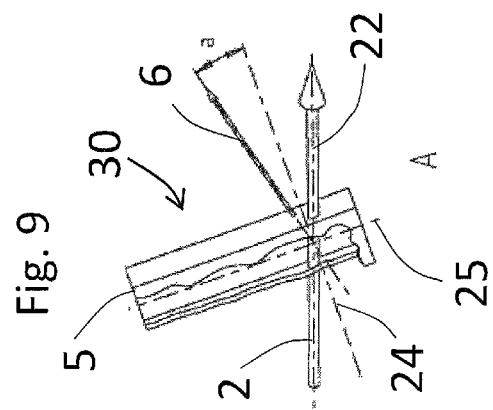

FIG. 5 illustrates an electromagnetic radiation beam geometry according to an exemplary embodiment of the invention for a cuboid sample container 5 and a forward scattering operation mode. FIG. 6 illustrates an electromagnetic radiation beam geometry according to an exemplary embodiment of the invention for a circular cylindrical sample container 5 and a forward scattering operation mode. FIG. 7 illustrates an electromagnetic radiation beam geometry according to an exemplary embodiment of the invention for a cuboid sample container 5 and a side scattering operation mode. FIG. 8 illustrates an electromagnetic radiation beam geometry according to an exemplary embodiment of the invention for a cuboid sample container 5 and a back scattering operation mode. FIG. 5 to FIG. 8 clearly show that the concept described above referring to FIG. 1 to FIG. 4 can be applied, mutatis mutandis, to different geometries of the sample container 5 and/or to different scattering detection architectures (i.e. the detection may be measured in transmission, back scattering or side scattering).

FIG. 9 to FIG. 13 illustrate different views of a relative orientation between an electromagnetic radiation beam and a sample container 5 of an apparatus 20 for analyzing a sample according to an exemplary embodiment of the invention.

It should be noted that the term "comprising" does not exclude other elements or steps and the "a" or "an" does not exclude a plurality. Also elements described in association with different embodiments may be combined.

Implementation of the invention is not limited to the preferred embodiments shown in the figures and described above. Instead, a multiplicity of variants are possible which use the solutions shown and the principle according to the invention even in the case of fundamentally different embodiments.

The invention claimed is:

1. An apparatus for analyzing a sample, the apparatus comprising:
   an electromagnetic radiation source configured for generating an incident electromagnetic radiation beam;
   a sample container configured for accommodating the sample to be analyzed, shaped to have a symmetry axis, arranged for receiving the incident electromagnetic radiation beam to propagate into the sample container for interaction with the sample, and arranged for enabling a scattered electromagnetic radiation beam, which is to be detected, to propagate out of the sample container; and an electromagnetic radiation detector configured for detecting the scattered electromagnetic radiation beam to be detected which is received from the sample container;

wherein the sample container is tilted with regard to a direction of the incident electromagnetic radiation beam so that an incident trajectory of the incident electromagnetic radiation beam directly before propagating into the sample container up to the symmetry axis is symmetric with respect to a scattered trajectory of the scattered electromagnetic radiation beam, which is to be detected, from the symmetry axis up to a position of the scattered electromagnetic radiation directly after having left the sample container, such that the scattered trajectory outside of the sample container is independent of a refraction index of the sample container and of the sample; and wherein the sample container is arranged with regard to a propagation direction of the incident electromagnetic radiation beam so that:

in a first viewing direction perpendicular to a plane including the symmetry axis of the sample container, the incident trajectory of the incident electromagnetic radiation beam and the scattered trajectory of the scattered electromagnetic radiation beam are arranged axially symmetrical to one another with regard to the symmetry axis of the sample container; and in a second viewing direction along the symmetry axis of the sample container, the incident trajectory of the incident electromagnetic radiation beam and the scattered trajectory of the scattered electromagnetic radiation beam are arranged axially symmetrical to one another.

2. The apparatus of claim 1, wherein the sample container is arranged so that, in the first viewing direction, the symmetry axis is tilted by an acute first tilting angle with regard to the propagation direction of the incident electromagnetic radiation beam along at least part of the incident trajectory.

3. The apparatus of claim 1, wherein the sample container is arranged so that, in the second viewing direction, a propagation direction of the scattered electromagnetic radiation beam along at least part of the scattered trajectory is arranged tilted by an acute second tilting angle with regard to at least part of the propagation direction of the incident electromagnetic radiation beam.

4. The apparatus of claim 2, wherein the first tilting angle is in a range between 75° and 89°, in particular in a range between 80° and 87°.

5. The apparatus of claim 3, wherein the second tilting angle is selected in a range between 2° and 30°, in particular in a range between 6° and 20°.

6. The apparatus of claim 1, wherein the sample container has a polygonal shape, particularly with a rectangular, more particularly quadratic, cross section, or has a cylindrical shape with a circular cross section, in a symmetry plane perpendicular to the symmetry axis, wherein a center of gravity of the polygon or circle is located on the symmetry axis.

7. The apparatus of claim 1, wherein at least a sample container's volume portion, which is arranged to be traversed by the electromagnetic radiation beam, has a constant cross sectional shape and area perpendicular to the symmetry axis.

8. The apparatus of claim 1, wherein the scattered electromagnetic radiation beam to be detected, which is propagating towards the electromagnetic radiation detector, is selected from a group consisting of a forward scattered electromagnetic radiation beam, a back scattered electromagnetic radiation beam, and a side scattered electromagnetic radiation beam, wherein in particular an angle between the incident electromagnetic radiation beam and the scattered electromagnetic radiation beam to be detected is in a range between 120° and 180°.

9. The apparatus of claim 1, comprising a mounting platform for mounting the sample container, wherein the mounting platform and the sample container are configured so that, when the sample container is mounted on the mounting platform, the symmetry axis is oriented parallel to the force of gravity.

10. The apparatus of claim 1, comprising a beam splitter configured for splitting electromagnetic radiation generated by the electromagnetic radiation source into a first part forming the incident electromagnetic radiation beam and into a second part forming a reference beam;

wherein the apparatus is configured for directing the reference beam to the electromagnetic radiation detector without interaction with the sample and is configured for bringing the scattered electromagnetic radiation beam to be detected and the reference beam into interference upstream of the electromagnetic radiation detector.

11. The apparatus of claim 1, when the apparatus is free of any compensation optics and any adjustment mechanism for compensating for different trajectories of scattered electromagnetic radiation beams downstream of the sample container, which different trajectories result from different values of the refraction index of different sample containers and/or different samples.

12. The apparatus of claim 1, configured as one of the group consisting of an Electrophoretic Light Scattering apparatus for measuring at least one of an electrophoretic mobility of the sample, and a zeta potential of particles in the sample, and a Dynamic Light Scattering apparatus for measuring a dimension of particles in the sample.

13. The apparatus of claim 1, comprising at least one feature of the group consisting of:

a source-sided beam manipulating element arranged between the electromagnetic radiation source and the sample container for manipulating the electromagnetic radiation beam upstream of the sample container to thereby direct the incident electromagnetic radiation beam tilted onto the sample container;

a detector-sided beam manipulating element arranged between the sample container and the electromagnetic radiation detector for manipulating the electromagnetic radiation beam downstream of the sample container to thereby direct the scattered electromagnetic radiation beam to be detected towards the electromagnetic radiation detector;

a backscatter detector configured for detecting electromagnetic radiation backscattered from the sample in the sample container;

the electromagnetic radiation source is configured for generating an incident light beam;

the electromagnetic radiation source is configured for generating an incident coherent electromagnetic radiation beam;

the electromagnetic radiation detector is configured as a photodetector;

the electromagnetic radiation detector is configured as a fiber optical detector;

the sample container is configured as a cuvette; and the sample container has a sample accommodation volume configured for accommodating the analyzed sample and being accessible via a top opening formed in the sample container.

14. A method of analyzing a sample, the method comprising:
   directing an incident electromagnetic radiation beam onto a sample container accommodating the sample to be analyzed and being shaped to have a symmetry axis;
   receiving the incident electromagnetic radiation beam by the sample container-to propagate into the sample container for interaction with the sample;
   enabling a scattered electromagnetic radiation beam, which is to be detected, to propagate out of the sample container;
   detecting the scattered electromagnetic radiation beam to be detected which is received from the sample container; and
   tilting the sample container with regard to a direction of the incident electromagnetic radiation beam so that an incident trajectory of the incident electromagnetic radiation beam directly before propagating into the sample container-up to the symmetry axis is symmetric with respect to a scattered trajectory of the scattered electromagnetic radiation beam, which is to be detected, from the symmetry axis up to a position of the scattered electromagnetic radiation beam directly after having left the sample container, such that the scattered trajectory outside of the sample container is independent of a refraction index of the sample container and of the sample;
   wherein the sample container is arranged with regard to a propagation direction of the incident electromagnetic radiation beam so that:
   in a first viewing direction perpendicular to a plane including the symmetry axis of the sample container, the incident trajectory of the incident electromagnetic radiation beam and the scattered trajectory of the scattered electromagnetic radiation beam are arranged axially symmetrical to one another with regard to the symmetry axis of the sample container; and
   in a second viewing direction along the symmetry axis of the sample container, the incident trajectory of the incident electromagnetic radiation beam and the scattered trajectory of the scattered electromagnetic radiation beam are arranged axially symmetrical to one another.

\* \* \* \* \*